(12) United States Patent
Ostgaard et al.

(10) Patent No.: US 7,246,527 B2
(45) Date of Patent: Jul. 24, 2007

(54) E-FIXTURE

(75) Inventors: Douglas R. Ostgaard, Bonney Lake, WA (US); Ramanlal A. Patel, Mukilto, WA (US); Lee A. McNeil, Mt. Vernon, WA (US)

(73) Assignee: The Boeing Company, Chicago, IL (US)

( * ) Notice: Subject to any disclaimer, the term of this patent is extended or adjusted under 35 U.S.C. 154(b) by 219 days.

(21) Appl. No.: 10/987,745

(22) Filed: Nov. 12, 2004

(65) Prior Publication Data

US 2006/0101921 A1 May 18, 2006

(51) Int. Cl.
*G01L 5/04* (2006.01)
(52) U.S. Cl. .......................................... 73/802; 73/159
(58) Field of Classification Search ................. 73/802, 73/794, 796, 798, 865.6, 533, 159
See application file for complete search history.

(56) References Cited

U.S. PATENT DOCUMENTS 2,383,491 A * 8/1945 Kemmer et al. ............... 73/798
5,065,630 A * 11/1991 Hadcock et al. ............... 73/802
6,487,902 B1 * 12/2002 Ghosh .......................... 73/159

* cited by examiner

*Primary Examiner*—Robert Raevis
(74) *Attorney, Agent, or Firm*—Ingrassia Fisher & Lorenz, P.C.

(57) ABSTRACT

A device and a method are disclosed for testing a curved panel assembly, which simulates a segment of an aircraft fuselage barrel section, subjected to combined loading. The device includes an axial load head assembly attached to the test panel assembly via one axial load fitting and configured to apply an axial load to the test panel assembly, and an axial-torsion reaction box connected to the axial load head assembly via linear journal bearing assemblies, where the axial-torsion reaction box is configured to be rotated by a pair of torsional loading systems to apply a torsional load to the test panel assembly. The device also includes a gore section attached to hoop load fittings of the test panel assembly, configured to provide degrees of freedom that constrain the test panel assembly to load and deflect as it would naturally in an actual fuselage barrel, form a plenum box to apply an internal pressure load, and provide hoop loading systems that complete the full hoop load application to the test panel assembly. A fixed reaction box attached to the test panel assembly via another axial load fitting rigidly attaches the test panel to the self-reacting frame, completing the internal load path of the overall system.

34 Claims, 12 Drawing Sheets

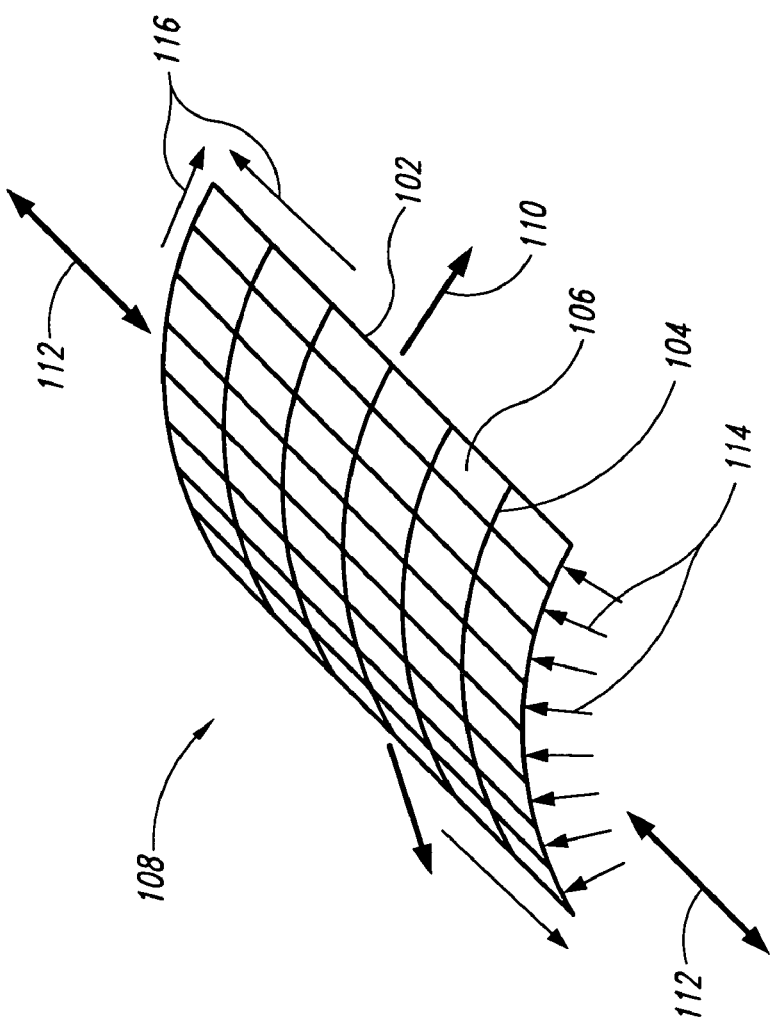
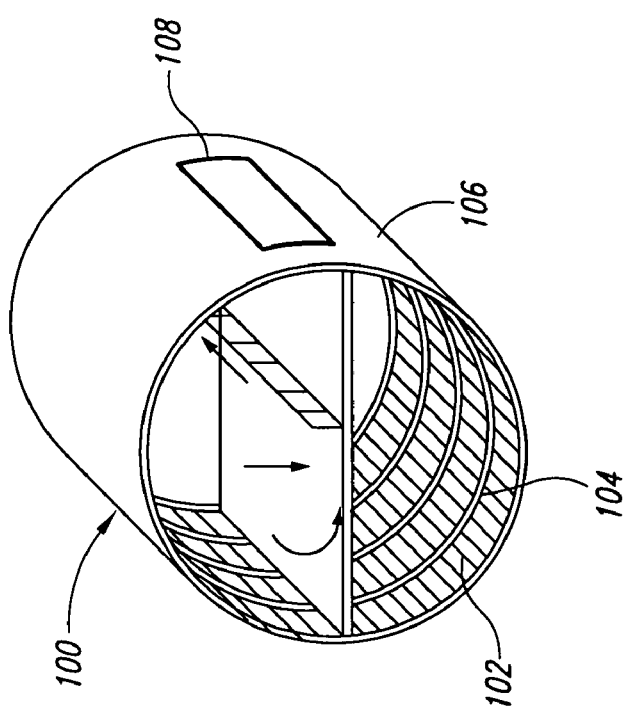
Fig. 1B
Fig. 1A

E-FIXTURE

BACKGROUND OF THE INVENTION

The present invention generally relates to a structural testing facility and, more particularly, to a testing facility for aircraft fuselage panels under various loading conditions.

During the past few decades, aircraft safety has been an important issue to design and maintenance engineers. Aircraft fuselage panels are subject to various types of loadings during normal operations and can develop cracks or failures by the process of fatigue. Such cracks grow slowly with increasing time and service, finally reaching a critical length of crack that can cause rapid propagation and catastrophic failure of an aircraft.

To understand and assess the effects of crack growth and residual strength of fuselage structures, several facilities have been developed to apply fight load conditions to large or full-scale models. For example, Rouse et al., AIAA paper No. 1423, 2003, discloses the Combined Loads Test (COLTS) facility at NASA Langley Research Center. In the COLTS facility, axial tension/compression combined with body torsion can be applied through moveable end platens to a curved stiffened fuselage panel. Also, internal pressurization develops partial hoop loading to simulate the cabin pressure. The segmented pressure box allows for torsional/axial displacement. However, the COLTS facility has the following characteristics: 1) an extensive FEM modeling is required to determine proper shear reaction, 2) it is difficult to develop full hoop loading in combination with torsion loading, and 3) the facility requires complex control algorithms.

Bakuckas, DOT/FAA/AR-01/46, discloses the Full-Scale Aircraft Structural Test Evaluation and Research (FASTER) facility at FAA William J. Hughes Technical Center. Using the FASTER facility, curved panels that are similar to a typical narrow-body fuselage structure consisting of skin, frames, shear clips, stringers, and either longitudinal splices or circumferential butt joints can be tested under biaxial tension loading. Also, discrete water actuated load systems are combined with internal air pressurization to develop full hoop loading. Shear stress can be applied to the periphery of a test panel via a cam actuated shear box. However, the FASTER facility fails to apply compression loading to the panel and the success of shear box performance may be questionable.

At http://www.ima-dresden.de/englisch/starteng.htm, the Curved Panel Test Fixture of IMA Gmhb Dresden has been disclosed. This facility can apply biaxial tensile loading to a curved panel via actuated load systems with internal air pressurization. However, it is not known whether the facility has the capability to load shear, compression loading or any combination thereof. A further example for panel testing facility can be found at Foster-Miller test Laboratory, Waltham, Mass. The D-Box test fixture of the Foster-Miller test laboratory can be used to test fuselage panels under biaxial tensile loading via actuated load systems with internal water pressurization. However, no attempt to apply full body loading has been made in that facility and test results are questionable.

D-Box test fixture for 777 Fuselage Development at Boeing Structures Test Laboratory, Seattle, Wash., is used to test fuselage panels under biaxial tensile loading due to internal air pressurization only. In that facility, the periphery of a test panel is rigidly attached to a pressure box. Also, this facility may need further development to accommodate the simulation of full body loadings. The Pie Fixture Test Facility at Northrop Grumman Structural Laboratory can test a fuselage panel under axial tension/compression combined with body torsion applied through moveable end platens. However, the facility has no internal pressurization mechanism, and therefore, cannot develop hoop loading. Also, it does not have any structure to develop proper shear reaction on the test panel.

A further example of panel testing facility is disclosed by Fields et al. at http://www.dfrc.nasa.gov/DTRS/2004/PDF/H-2488.pdf. As disclosed by Fields et al., the "Combined Loads Test Fixture for Thermal-Structural Testing Aerospace Vehicle Concepts" at Dryden Flight Research Center can test a uni-axial loaded flat panel with shear introduced through a "picture" frame. The panel may be subject to thermal conditioning from room temperature to 915° F. However, the facility cannot apply pressure or hoop loads as the test panels are flat. A still further example for panel testing facility is the Cryogenic Pressure Box Test facility at NASA Langley Research Center, as disclosed by Glass et al. at http://techreports.larc.nasa.gov/ltrs/PDF/2003/aiaa/NASA-aiaa-2003-1423.pdf. The Cryogenic Pressure Box can test a bi-axial loaded curved panel under cryogenic conditioning. However, this facility has not been known to test the panel under controlled pressure, hoop, or shear loading.

As is well known, aircraft fuselage panels are subject to one or more loads during normal operation, where the loads may include hoop load due to internal cabin pressure, longitudinal load (or, equivalently, axial tension/compression load), torsion and shear loads. As existing panel facilities can partially simulate these loads, there is a need for a facility that has a capability to simulate these loadings, either individually or in combination thereof, and that can test curved fuselage panels under more realistic flight loading conditions.

SUMMARY OF THE INVENTION

The present invention provides a common fixture, named E-Fixture, for testing curved fuselage skin-stringer-frame panels under realistic flight loading conditions. The E-Fixture has the capability of applying tension, compression, shear via body torsion, and pressure loads to a test panel in various combinations thereof to evaluate the ultimate static strength and fatigue spectrum loading performance of aircraft fuselage panels. The E-Fixture has the capability of applying combined static, fatigue and thermal loadings. Provisions for fast turn-around of test panel installation and testing, and accommodation of test panels with varying combinations of skin-stringer gages and lay-ups are incorporated in the design.

In one aspect of the present invention, a device for testing a test panel assembly simulating an aircraft fuselage barrel section includes: an axial load head assembly attached to the test panel assembly via a first axial load fitting and configured to apply an axial load to the test panel assembly; an axial-torsion reaction box connected to the axial load head assembly via a plurality of linear journal bearing assemblies, the axial-torsion reaction box configured to be rotated by a pair of torsional loading systems to apply a torsional load to the test panel assembly; a gore section attached to a plurality of hoop load fittings of the test panel assembly and configured to apply an internal pressure load and a hoop load to the test panel assembly; and a fixed reaction box attached to the test panel assembly via a second axial load fitting and configured to remain stationary during application of loads.

In another aspect of the present invention, a device for testing a test panel assembly simulating an aircraft fuselage barrel section includes: an axial load system for generating and applying an axial load to the test panel assembly; an axial load head connected to the axial loading system, the axial load head having an axial load fitting interface and a pair of over-pressure assembly portings; an axial-torsion reaction box connected to the axial load head assembly via a plurality of linear journal bearing assemblies, the axial-torsion reaction box configured to be rotated by a pair of torsional loading systems to apply a torsional load to the test panel assembly; a gore section attached to a plurality of hoop load fittings of the test panel assembly and configured to apply an internal pressure load and a hoop load to the test panel assembly; and a fixed reaction box attached to the test panel assembly via a second axial load fitting and configured to remain stationary during application of loads.

In still another aspect of the present invention, a device for testing a test panel assembly simulating an aircraft fuselage barrel section includes: an axial load system for generating axial load; an axial load head connected to the axial loading system, the axial load head having an axial load fitting interface and a pair of over-pressure assembly portings; an axial-torsion reaction box connected to the axial load head assembly via a plurality of linear journal bearing assemblies, the axial-torsion reaction box configured to be rotated by a pair of torsional loading systems to apply a torsional load to the test panel assembly; and a gore section attached to a plurality of hoop load fittings of the test panel assembly and configured to apply an internal pressure load and a hoop load to the test panel assembly. The gore section comprises: a plurality of gore section frame assemblies rotatably connected to a gore pivot base; a plurality of hoop load clevis fittings, each said hoop load clevis fitting attached to one of the plurality of gore section frame assemblies; a plurality of hoop load actuators mounted on one of the plurality of gore section frame assemblies; a plenum box assembly located between the test panel assembly and the plurality of gore section frame assemblies; a plurality of hoop stop assemblies, each said hoop stop assembly mounted on one of the plurality of gore section frame assemblies; a plurality of counter-weights for compensating weight of the plurality of gore section frame assemblies; and a plurality of counter-balance attachment connected to the plurality of counter-weights via a plurality of wire ropes and attached to one of the plurality of gore section frame assemblies. The device also includes: a fixed reaction box attached to the test panel assembly via a second axial load fitting and configured to remain stationary during application of loads; and a structural self-reacting frame having a plurality of truss structures. The structural self-reacting frame comprises: a fixed reaction bulkhead assembly secured to one of the plurality of truss structure; an aft radial-thrust pivot bearing support located on a first one of the plurality of truss structures; a forward radial pivot bearing support located on a second one of the plurality of truss structures; a torsion system support structure secured to a third one of the plurality of truss structures; a removable cross-brace assembly coupled to a fourth one of the plurality of truss structures; the gore pivot base secured to a fifth one of the plurality of truss structures; and a structural diaphragm located under the gore pivot base.

In yet another aspect of the present invention, a method for applying combined loadings to a test panel assembly to simulate airframe real flight loads on a fuselage barrel section includes steps of: loading a test panel assembly to a test fixture; applying an air pressure to the loaded test panel assembly via a plenum box assembly of the test fixture to simulate an real internal cabin pressure; applying a circumferential hoop load to the loaded test panel assembly via a gore section of the test fixture to simulate an real internal cabin pressure; applying an axial load to the loaded test panel assembly via an axial loading system to simulate a real axial load; and applying a shear load to the loaded test panel assembly via an axial-torsion reaction box to simulate a real shear load.

In another aspect of the present invention, a test panel assembly comprises: a curved panel having two axial composite edge bands and two radial composite edge bands, the two axial composite edge bands potted and connected to the first and second axial load fittings, respectively; the plurality of hoop load fittings attached to the two radial composite edge bands; a plurality of bonded pads attached to the curved panel; a plurality of frames secured to the curved panel; a plurality of stringers secured to the curved panel; a plurality of frame transition fittings for securing the plurality of frames to the curved panel; and a plurality of steel doublers attached to corners of the curved panel.

These and other features, aspects and advantages of the present invention will become better understood with reference to the following drawings, description and claims.

BRIEF DESCRIPTION OF THE DRAWINGS

FIG. 1A is a schematic diagram of a fuselage barrel section of a conventional aircraft;

FIG. 1B is a schematic diagram of a test panel taken from the fuselage barrel section shown in FIG. 1A, which may be tested using the present invention;

DETAILED DESCRIPTION OF THE INVENTION

Figure 2:
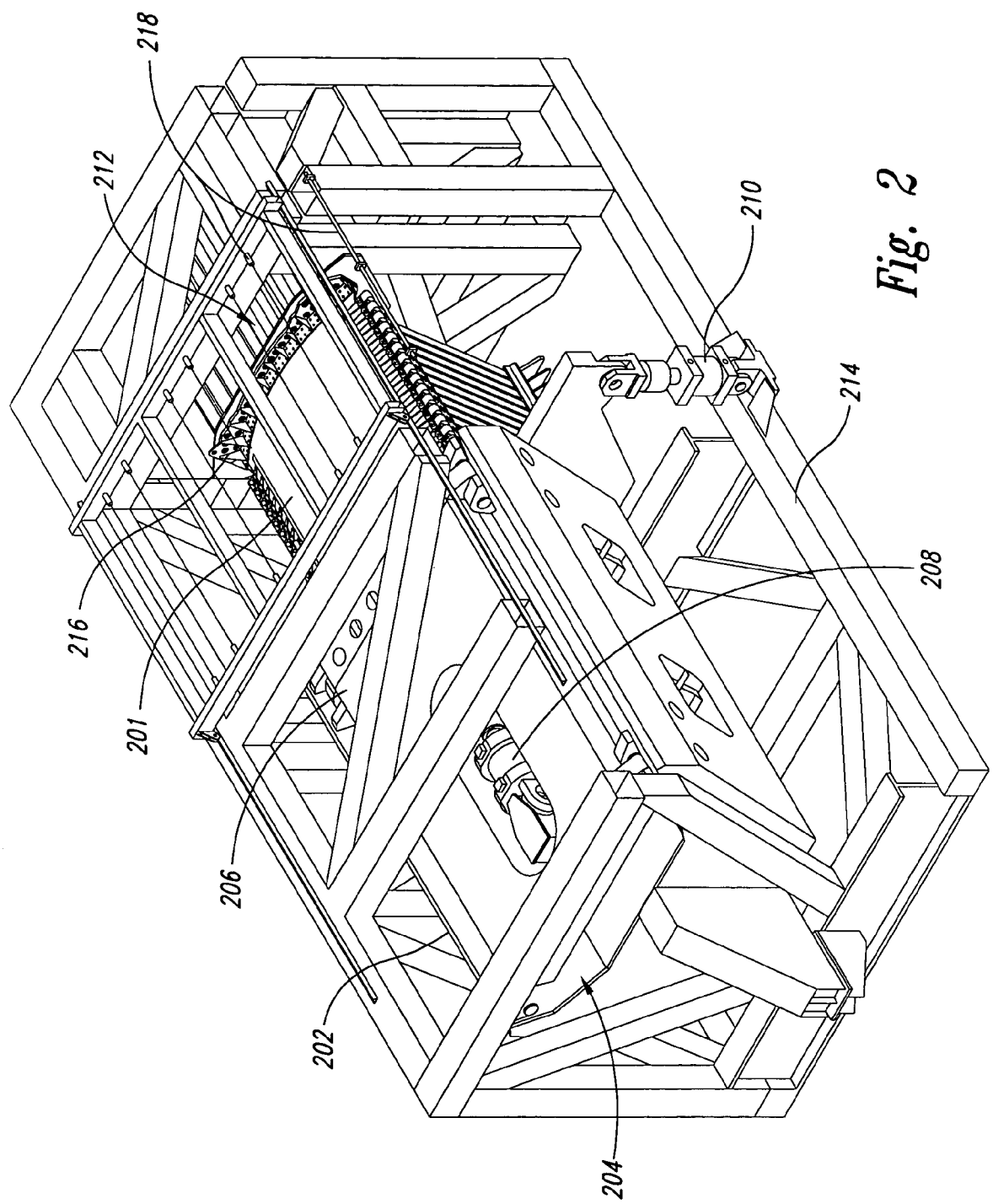
FIG. 2 is an overall installation view of the E-Fixture in accordance with one embodiment of the present invention.

The following detailed description is of the best currently contemplated modes of carrying out the invention. The description is not to be taken in a limiting sense, but is made merely for the purpose of illustrating the general principles of the invention, since the scope of the invention is best defined by the appended claims.

Broadly, the present invention provides a test fixture, called the "E-Fixture", for testing curved fuselage panels to support design and analysis of aircraft fuselage development. Unlike the existing test fixtures, the E-Fixture has the capability of simultaneously applying tension, compression, shear, hoop and pressure loads, individually or in combination, to the test panel to evaluate the ultimate static strength and fatigue spectrum loading performance of aircraft fuselage panels. Such a capability can validate design/analysis methods for combined loadings of pre- and post-buckled curved fuselage panels, which is critical to the evaluation of fuselage performance. The combined loading capability of the E-Fixture enables the simulation of, but is not limited to, post buckled states, shear compression buckling, ultimate tension and pressure loads, fatigue spectrum loads, damage tolerance, environmental conditioning, and repair evaluation.

FIG. 1A is a schematic diagram of a fuselage barrel section 100 of a conventional aircraft. As illustrated in FIG. 1A, the fuselage barrel section 100 comprises stringers 102, frames 104 and skins 106. Typically, a panel segment 108 of the fuselage barrel section 100 may be sampled and tested in a test fixture. FIG. 1B is a schematic diagram of the panel segment 108 taken from the fuselage barrel section 100 shown in FIG. 1A, which can be tested using the present invention.

As illustrated in FIG. 1B, the segment 108 may be subject to different types of loads during the normal operation of the aircraft. Typically, panel loading may include hoop loads 110 due to internal pressure 114, axial tension/compression loads due to bending 112, and shear loads 116 due to torsion. The internal pressure 114 may stem from the pressure difference between the cabin and ambient pressures. The hoop loads 110, more specifically hoop stress σ, may be calculated by an equation $\sigma = PR/t$, where P is the internal pressure 114, R is the radius of the fuselage barrel section 100 and t is the thickness of the panel 106. In one embodiment, the dimension of the segment 108 to be tested may be 116" long and 108" wide and include 5 frames and 9 stringers. It is noted that the any number of stringers and frames may be practiced without deviating from the present teachings.

FIG. 2 is an overall installation view of the E-Fixture 200 in accordance with one embodiment of the present teachings. The E-Fixture 200 may test a panel assembly 201 that may simulate a segment of the fuselage barrel 108. The E-Fixture 200 may comprise: an axial-torsion reaction box 202; an axial load head assembly 204 mounted on the axial-torsion box 202, the axial load head assembly 204 including an axial load head 206 and an axial loading system 208; a pair of torsional loading systems 210; a fixed reaction box 212; a structural self-reacting frame 214 for supporting all the elements of the Fixture 200; a pair of axial load fitting 216 attached to the fixed reaction box 212 and the axial load head 206; failure containment screens 218; and a segmented gore section assembly 220 mounted on a gore pivot base 224 (shown in FIG. 3). For the purpose of illustration, a near side portion of the structural self-reacting frame 214 is not shown in FIG. 2. Further details of the structural self-reacting frame 214 will be given in FIG. 13.

As will be explained, the E-Fixture 200 may apply combined loadings to realistically simulate airframe flight loads in the following manner: 1) internal cabin pressure 114 via regulated air pressure; 2) circumferential hoop loads 110 via hydraulic actuated load systems and the regulated air pressure; 3) axial loads 112 (tension or compression) via a guided hydraulic actuated load system; and 4) shear loads 116 (torsional) via hydraulic actuated load systems.

Figure 3:
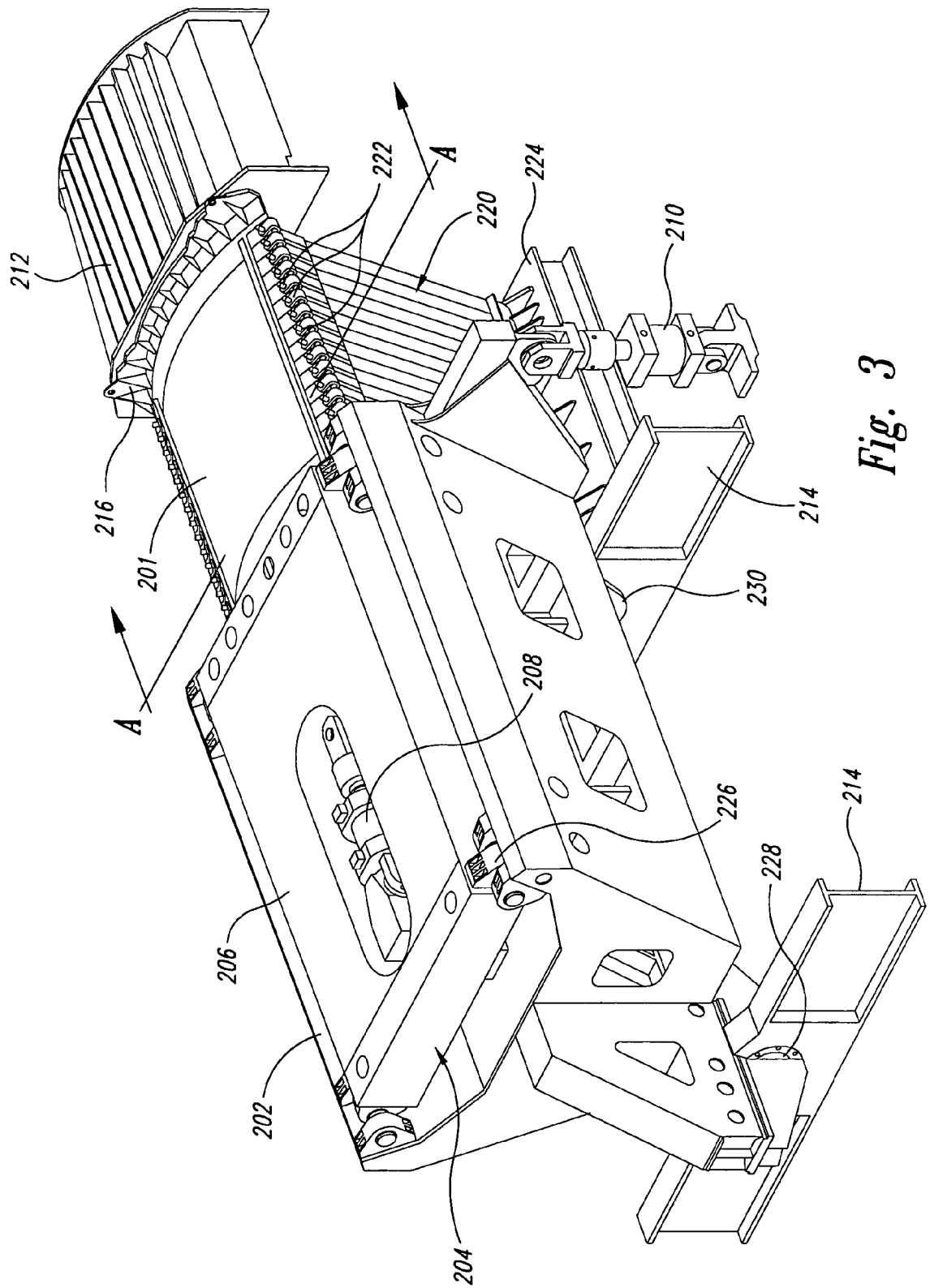
FIG. 3 shows the E-Fixture of FIG. 2 without its structural self-reacting frame.

FIG. 3 shows the E-Fixture 200 without its structural self-reacting frame. For the purpose of clarity of illustration, most of the structural self-reacting frame 212 is not shown in FIG. 3. As shown in FIG. 3, hoop load fittings 222 may be mounted on the free edge of the test panel assembly 201 in the circumferential direction. The axial load head assembly 204 may be constrained to pure linear movement in the axial direction of the test panel assembly 201 by linear journal bearing assemblies 226. The axial-torsion reaction box 202 may be mounted on the structural self-reacting frame 214 using radial-thrust roller bearings 228 and radial pivot roller bearings 230.

Figure 4:
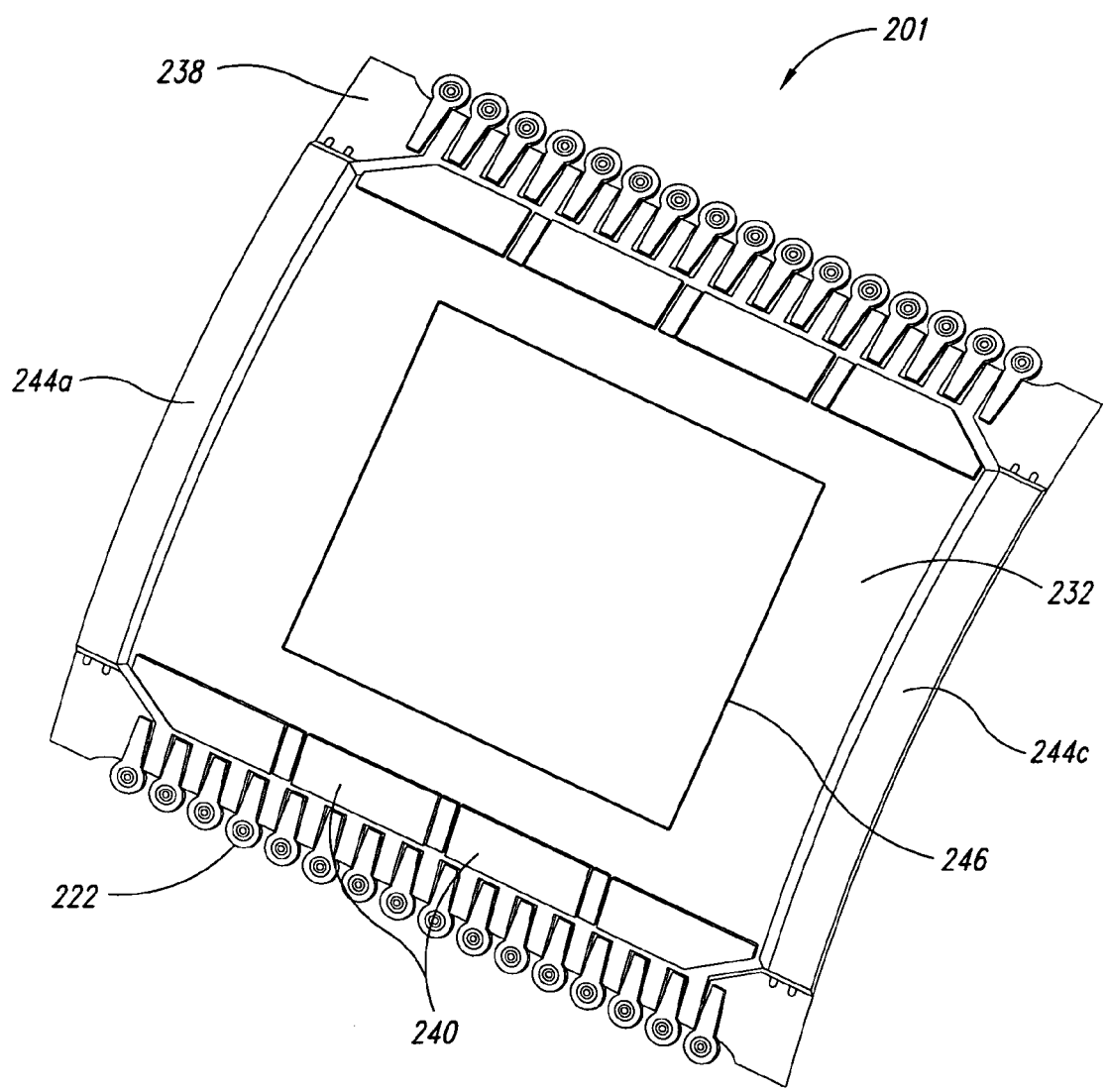
FIG. 4 is an outside mold line (OML) view of a test panel assembly in accordance with one embodiment of the present invention.
Figure 5:
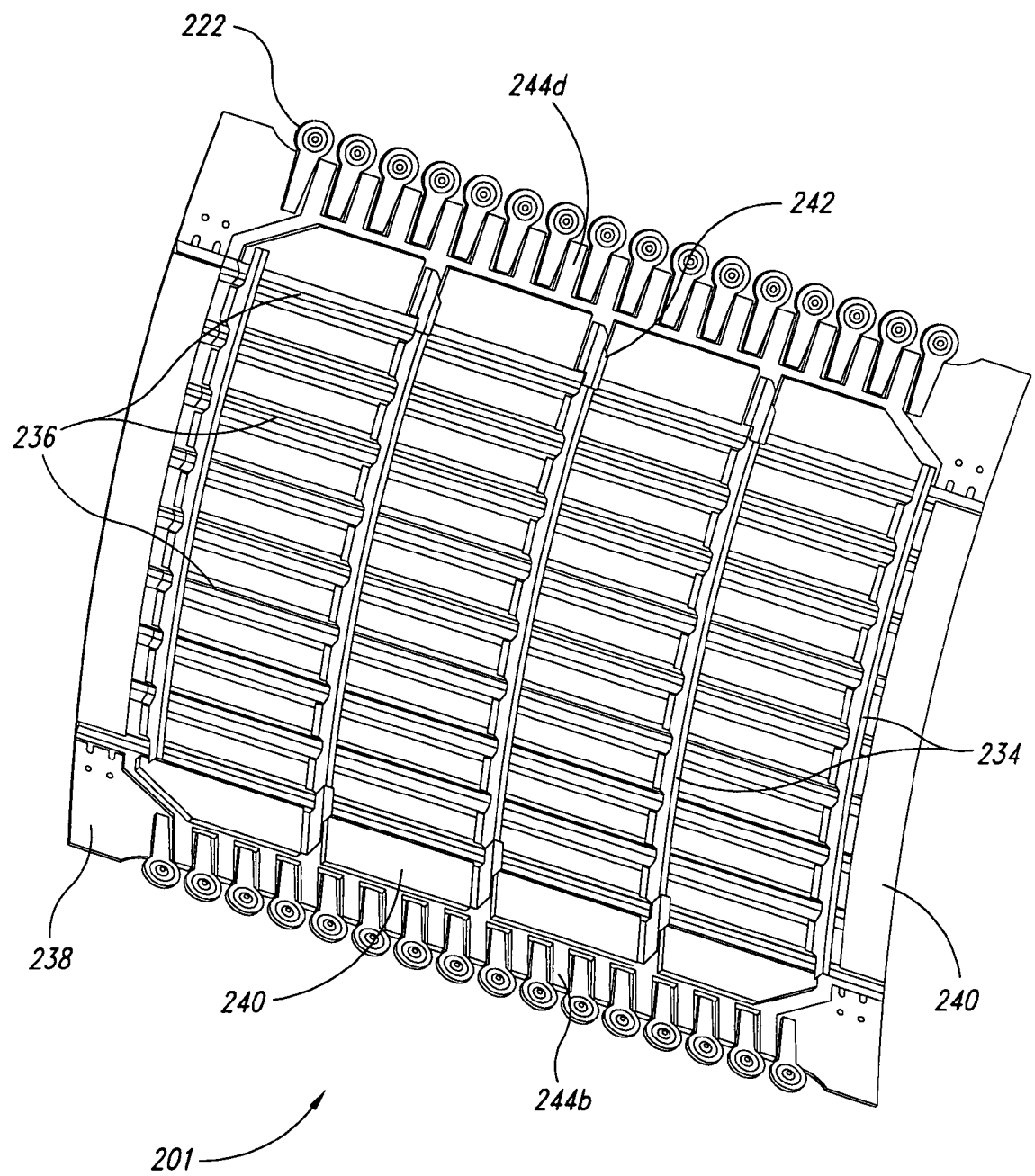
FIG. 5 is an inside mold line (IML) view of the test panel assembly of FIG. 4.

FIGS. 4–5 are outside mold line (OML) and inside mold line (IML) views of the typical test panel assembly 201, respectively. As illustrated in FIGS. 4 and 5, the test panel assembly 201 may comprise a curved panel 232; frames 234; stringers 236; bonded steel doublers 238 that are attached to preferably each corner of the curved panel 232 on both internal and external sides; bonded pads 240; hoop load fittings 222 to be coupled to the segmented gore section assembly 220; and frame transition fittings 242 for securing both ends of the frames 234 to the curved panel 232. Four composite edge bands 244a–d may be formed near the four edges of the test panel assembly 201. Especially, the fore and aft ends 244a and 244c may be potted with epoxy resins to provide void fill between panel and fitting.

The design of the test panel assembly 201 may incorporate important features necessary for the successful application of shear via the pair of torsional loading systems 210. The test panel assembly 201 may have a larger dimension than the representative test area 246 that may correspond to the fuselage barrel segment 108. The composite edge bands 244a–d and local reinforcements, such as frames 234 and stringers 236, may be designed to replicate the behavior of a complete barrel section 100. Detailed finite element analysis may be necessary to refine the design to match this behavior.

The hoop load fittings 222 may attach to the curved panel 232 independently so as not to stiffen the test panel 232 axially, but allow the panel to deflect circumferentially and axially under combined loads. Each of these load hoop fittings 222 may contain a spherical bearing at the curved panel 232 coupled to the test fixture interface. This spherical bearing interface may allow for rotation at the pinned joint to eliminate the possibility of a local moment developing in the curved panel 232 during pressurization. Hoop edge attachment designs for this type of test fixture have historically been one of the primary difficulties in achieving a representative panel test. The curved panel 232 must be substantially connected to the E-Fixture 200 without influencing the stiffness, and thus the performance of the test panel assembly 201. The test panel assembly design utilized in the E-Fixture 200 is an integral part of the overall test fixture performance.

As mentioned, the fore and aft ends 244a and 244c of the curved test panel 232 may be potted to reduce the complexity of the fittings that interface the test panel assembly 201 to the fixed reaction box 212 and the axial load head 206. Potting may eliminate the irregular surface that may exist due to the stringer bay geometries. Because the ends of the curved panel 232 may be highly loaded, no attempt may be made to incorporate radial freedom of the curved panel 232. These ends 244a and 244c may be rigidly attached to the E-Fixture 200 via bolted connections at the axial load fittings 216. Extra panel length may be used to transition from the rigid connection to the representative test area 246. Fittings may be added to the panel frames 234 to attach frame pre-tensioning devices.

Figure 6:
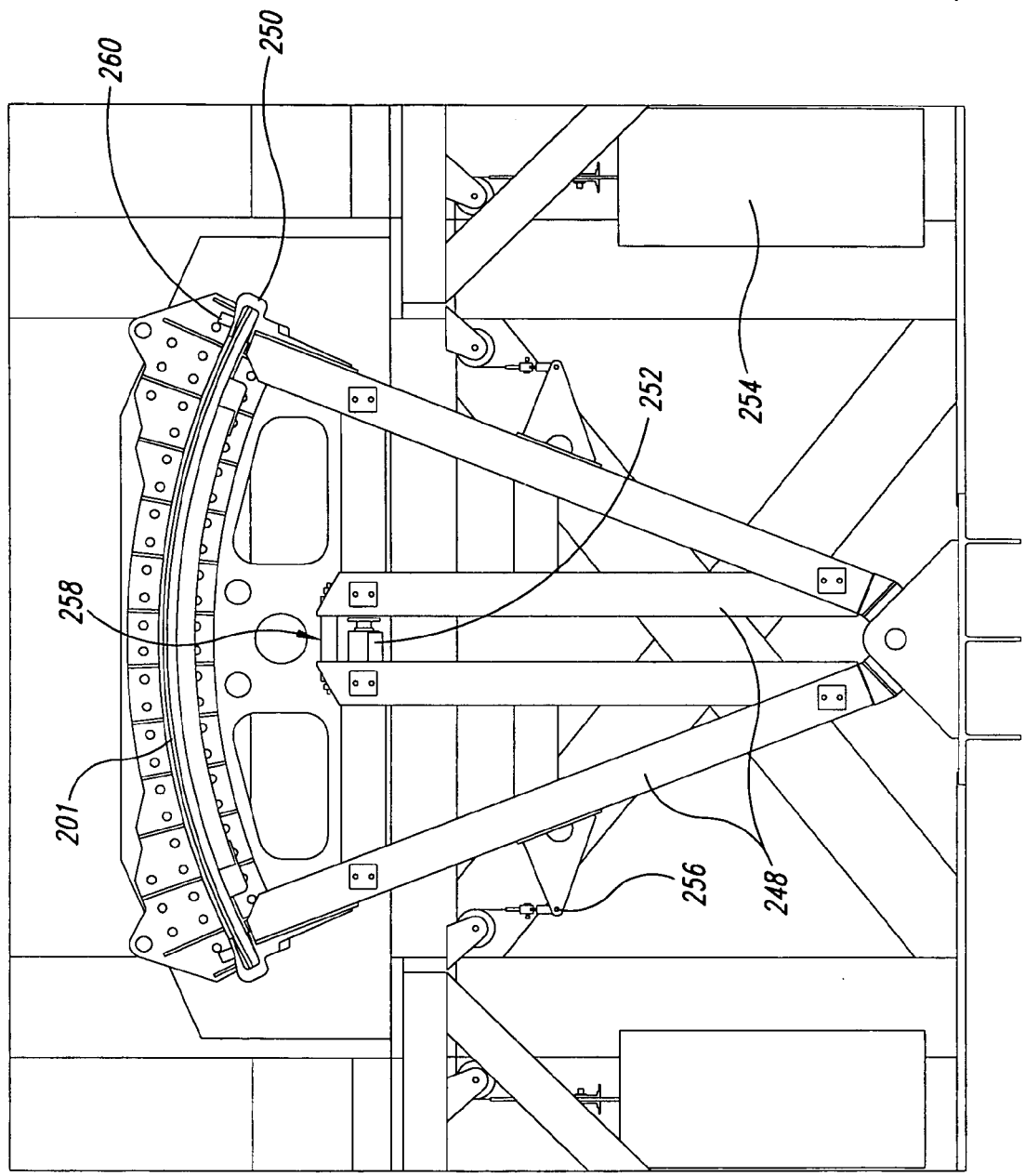
FIG. 6 is a partial cross-sectional view through the gore section taken along the line A—A of FIG. 3.

FIG. 6 is a partial cross-sectional view through the segmented gore section assembly (or, briefly, "gore section") 220 taken along the line A—A of FIG. 3. The "gore section" is a reference to a pie shaped segment of a barrel section volume. The gore section 220 may comprise: a series of paired gore section frame assemblies 248 that are pinned to each other via a pivot pin at the gore point; hoop load clevis fittings 250; hoop load actuators 252; counter-weights 254 for compensating the weight of gore section frame assemblies 248; a plurality of counter-balance attachment 256; a plenum box assembly 300 (shown in FIG. 12) located between the test panel assembly 201 and the top of the gore section frame assemblies 248; and hoop stop assemblies 258. The gore section assembly 220 may be designed with degrees of freedom that allow the test panel assembly 201 to behave as it would naturally in an actual fuselage barrel 100.

Each pair of gore section frame assemblies 248 may be free to rotate about the pivot independently. Each of the hoop load clevis fittings 250 may be mounted to the end of the radial member of each frame assembly 248 and provide the panel pinning interface, in which each of the hoop load fittings 222 may engage. Calibrated load pins 260 may be used to pin the hoop load fitting 222 on the test panel assembly 201, to the hoop load clevis fitting 250 on each gore section frame assembly 248. The load pin 260 may be indexed to the clevis fittings 250 to ensure correct orientation. These load pins 260 may provide a discrete hoop load measurement at each interface. In one embodiment, the axial fittings 216 may be fastened with structural bolts in a typical aircraft structural connection, such as Class 1 connection as known in the art. In another embodiment, the holes in the test panel assembly 201 may be match-drilled from existing holes in the axial load fittings 216. In this operation, undersized bushings in the lower axial load fittings 216 and the holes in the test panel assembly 201 are machined together to ensure a proper fit. These bushings may be replaced prior to each test panel installation. In yet another embodiment, dowel pins may be used to relocate the axial load fittings 216 for subsequent panel installations.

Figure 7:
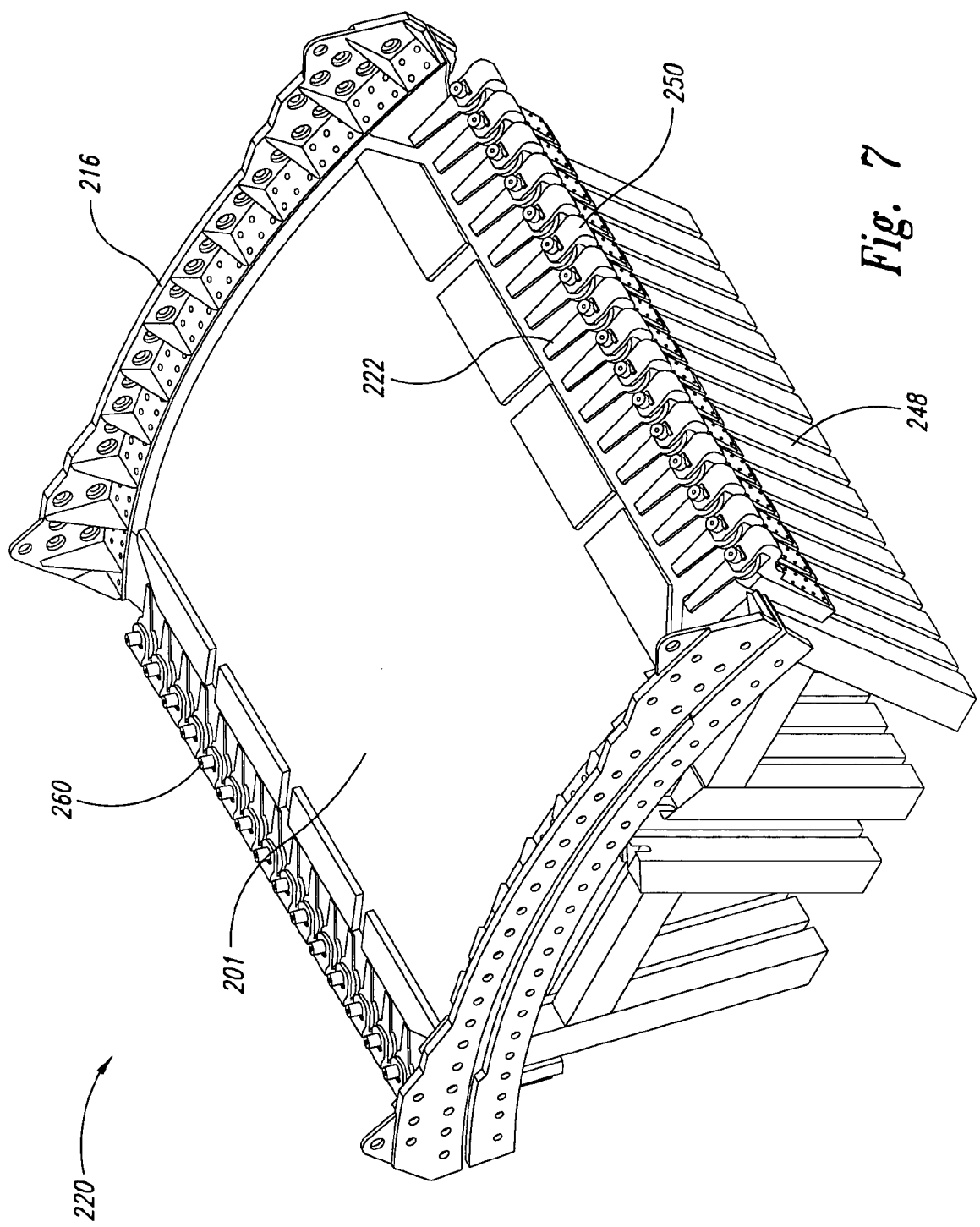
FIG. 7 is a perspective view of the gore section shown in FIG. 6.

FIG. 7 is a perspective view of the gore section 220 shown in FIG. 6. As shown in FIG. 7, the test panel assembly 201 may be held by two axial load fittings 216 and a number of hoop loading fittings 222 coupled to the hoop load clevis fittings 250. Because the applied hoop load may work through the gore section frame assemblies 248, which may be constrained by pivots at the gore point, the hoop load may be truly circumferential in nature. In contrast, the panel test fixture predecessors apply tangential loads along the panel periphery. This distinction may be important with large edge deflections since a tangentially applied load in the fixture predecessors will tend to pull the curved shape out of the test panel assembly 201.

Figure 8:
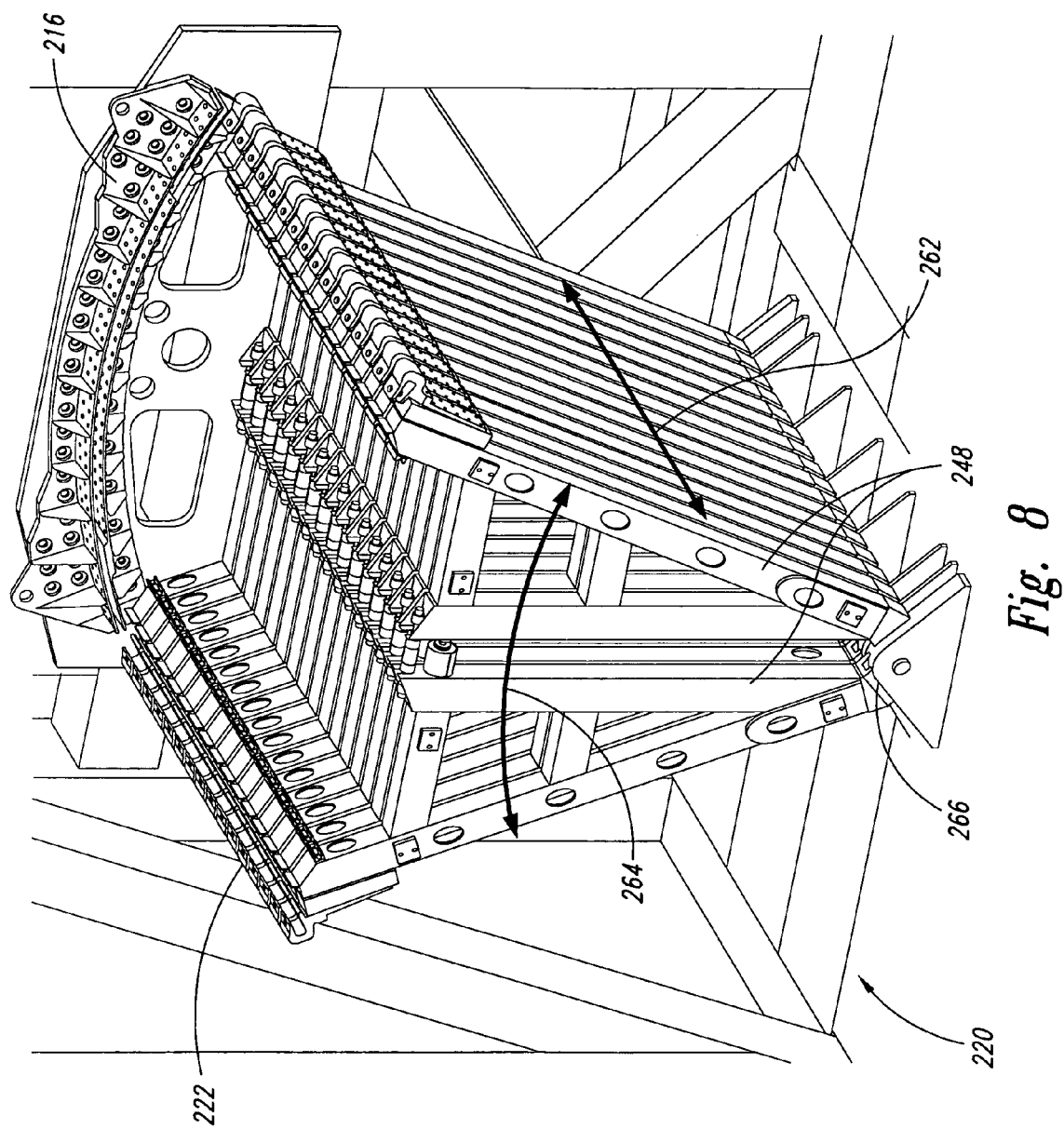
FIG. 8 is a perspective view of the gore section of FIG. 7, without a test panel assembly, illustrating the provisioned degrees of freedom.

FIG. 8 is a perspective view of the gore section 220 of FIG. 7, without the test panel assembly 201 illustrating the provisioned degrees of freedom. As illustrated in FIG. 8, the gore section 220 may be designed to behave as a bellows that is free to deflect axially and circumferentially as indicated by arrows 262 and 264, respectively. The gore section frame assemblies 248 may slide and rotate about the pivot pin at the gore point, which is the center-of-radius of the test panel assembly 201. The pivot pin may also structurally connect the gore section frame assemblies 248 to the gore pivot base 224, which is structurally connected to the structural self-reacting frame 214. Since the curved test panel is rigidly attached to the fixed reaction box 212 through the axial load fittings 216, the gore section 220 expands and compresses from that stationary end to the free end at the axial load head 206. The largest relative frame movements are located at this free end.

Figure 9:
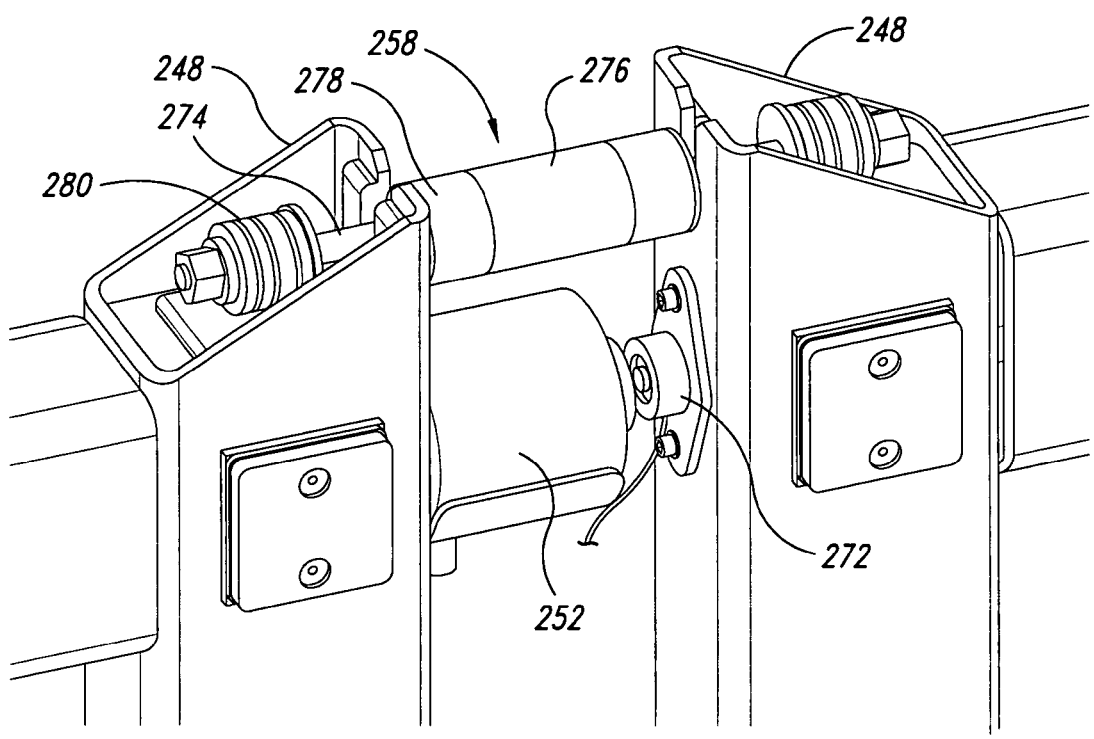
FIG. 9 is an enlarged perspective view of the hoop stop assembly and hoop loading system shown in FIG. 6.

FIG. 9 is an enlarged perspective view of the hoop stop assembly 258 and hoop loading system 252 shown in FIG. 6, where each hoop stop assembly 258 and hoop loading system 252 may be mounted on a gore section frame assembly 248. As illustrated in FIG. 9, the hoop stop assembly 258 may include a stop tube 276, a pair of elastomeric die springs 278; a pair of progressive stop disc spring assemblies 280. The hoop load actuators 252, mounted between each pair of gore section frame assemblies 248, may apply a spreading force to the pair to supplement the hoop forces generated by air pressurization of the plenum cavity formed inside of the plenum box assembly 300 (shown in FIG. 12).

The hoop load actuators 252 may be low-profile hydraulic actuators and work in consort with the pneumatic control valve to apply representative hoop loading to the test panel assembly 201. Each hoop load actuator 252 may be connected to one of two manifolds so that a single pressure source may control each group of the actuators 252 simultaneously, or they may be configured for discrete control. The hoop load actuators 252 on gore section frame assemblies 248 adjacent to the test panel frames 234 may be controlled by one source, with the balance by the other. The load pins 260 at the hoop clevis interface may provide feedback to the control system, to determine the proper composite inputs from the resultant hoop loads due to air pressurization, and the hydraulically actuated hoop load actuators 252. Calibrated load buttons 272 mounted on the opposing side of the hoop load actuators 252 may be used to monitor the performance of the hoop load actuators 252.

Each pair of gore section frame assemblies 248 may be linked, above its actuator 252, by the hoop stop assembly 258. The hoop stop assembly 258 may comprise a stop tube 276; a pair of elastomeric die springs 278; a pair of progressive stop disc spring assemblies 280; and a bar element 274 disposed along the longitudinal axis of the stop tube 276, the pair of elastomeric die springs 278 and the pair of progressive stop disc spring assembly 280. The hoop stop assembly 258 may limit the relative circumferential travel of the gore section frame assembly 248, and provide a soft stop feature at each limit. In the advent of a panel failure, the hoop stop assembly 258 may prevent the gore section frame assembly 248 from over travel. The progressive stop disc spring assembly 280 may decelerate the dynamic gore section frame assembly 248. The elastomeric die springs 278 may protect the calibrated load buttons 272 from damage during the recoil. Under normal loading, the hoop stop assembly 258 may not engage the gore section frame assemblies 248, and they are readily removable to facilitate panel installation.

Figure 10:
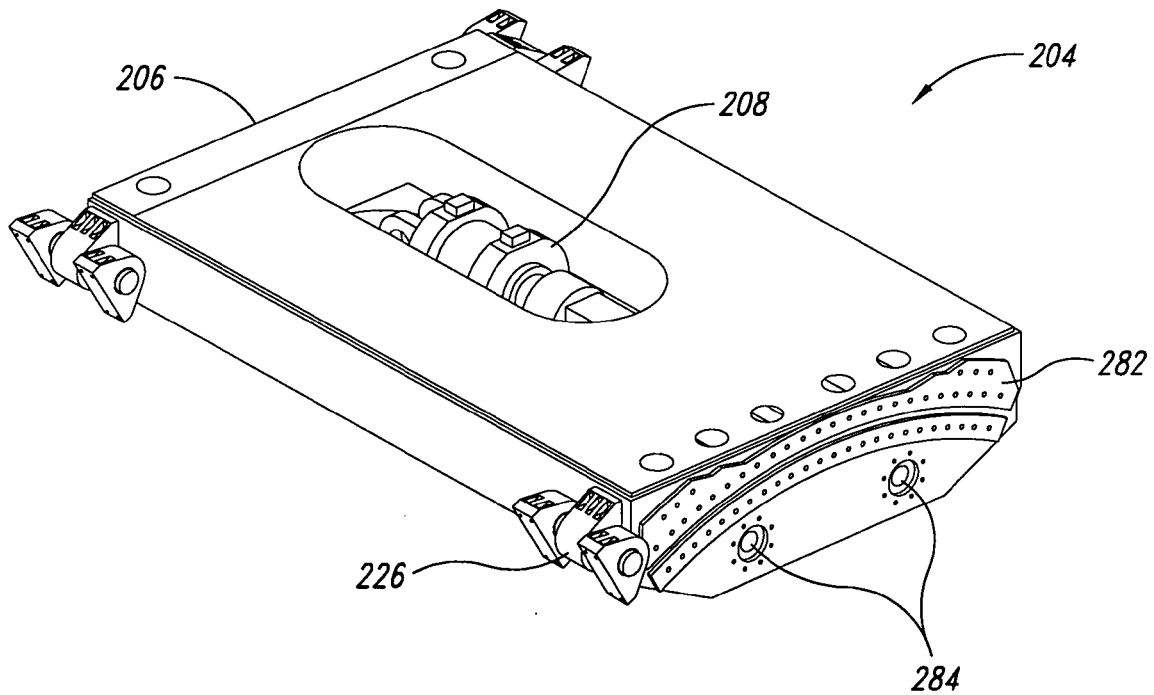
FIG. 10 is a perspective view of the axial load head assembly shown in FIG. 3.

FIG. 10 is a perspective view of the axial load head assembly 204 shown in FIG. 3. As illustrated in FIG. 10, the axial load head assembly 204 may comprise the axial load head 206, axial loading system 208 and two over-pressure assembly portings 284. The axial tension/compression load may be applied to the curved test panel assembly 201 via the axial load head 206 that may be a sliding box structure. The axial load head 206 may provide a stiff machined axial load fitting interface 282 for the axial load fitting 216 mounted on the free end of the test panel assembly 201. The axial load head 206 may be constrained to pure linear movement in the axial direction of the test panel assembly 201 by linear journal bearing assemblies 226 mounted to the axial-torsion reaction box 202. The linear journal bearing assemblies 226 may be sized to react the loads due to the applied torsion. The journal assemblies 226 may incorporate low friction sleeve bearings to minimize the development of parasitic friction loads.

The axial load head 206 may surround the axial loading system 208 to minimize the footprint of the test fixture. The internal structure of the axial load head 206 may be matched to that of the fixed reaction box 212 to ensure similar reaction characteristics at each end of the test panel assembly 201. The face of the axial load head 206 may also serve as the closure plate for the air pressurization plenum box assembly 300 (shown in FIG. 12). Two penetrations may provide porting 284 for the over-pressure, frangible disk assemblies.

Figure 11:
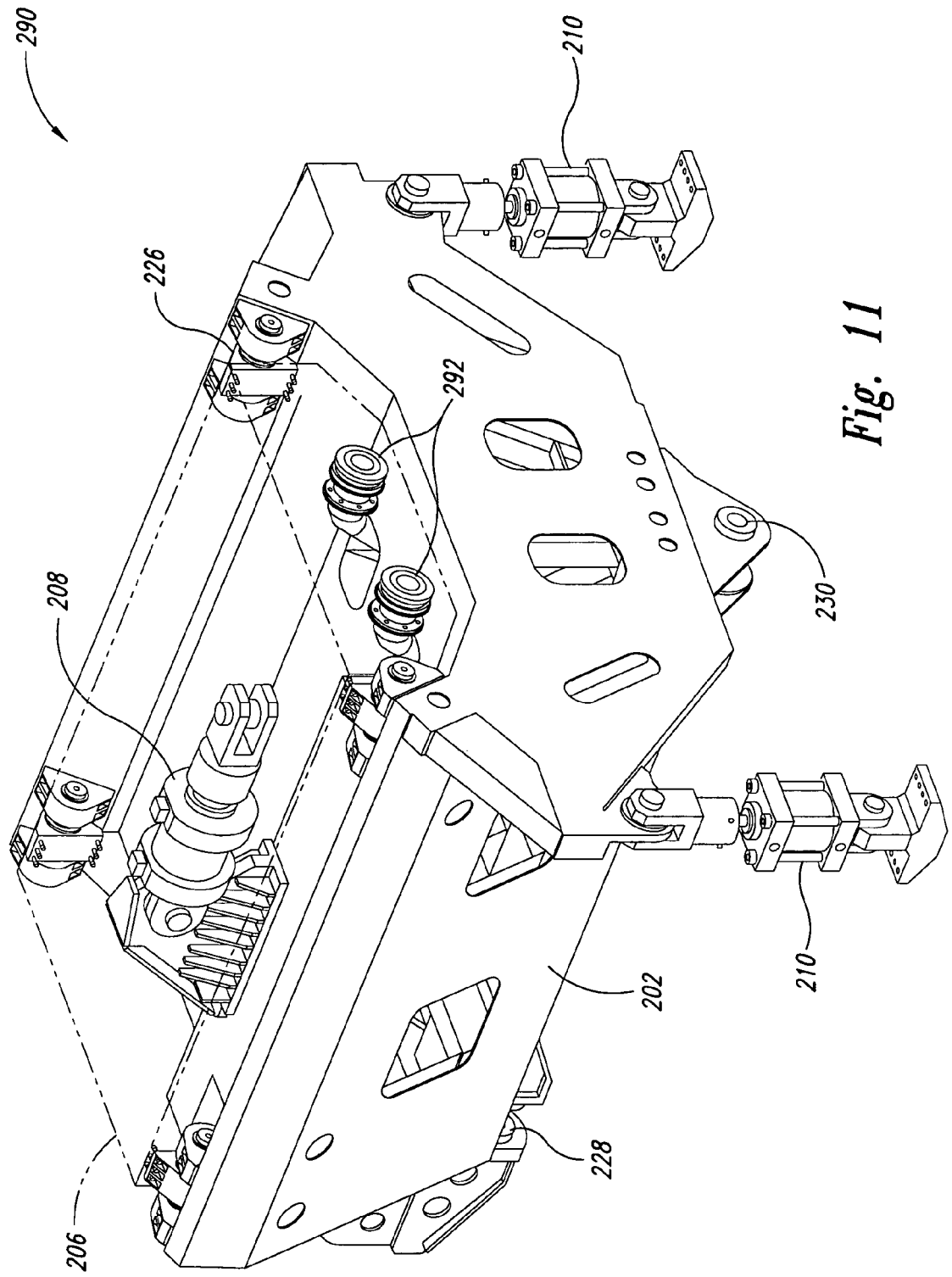
FIG. 11 is a perspective view of the axial-torsion reaction box and load systems of the E-Fixture of FIG. 2.

FIG. 11 is a perspective view of the axial-torsion reaction box and load systems 290 of the E-Fixture 200. As illustrated in FIG. 11, the axial-torsion reaction box and load systems 290 may comprise the axial load head assembly 204; axial-torsion reaction box 202; over-pressure frangible rupture disk assemblies 292 coupled to the over-pressure assembly portings 284 (shown in FIG. 10); linear journal bearing assemblies 226; and torsional loading systems 210.

The axial-torsion reaction box 202 may be designed to rotate about a single pivot axis located at the centerline of the curved test panel radius. This rotating box consists of center truss beam, surrounded by a shell structure. Load anchor lugs may mount to the base of the center truss. The forward pivot pin joint may carry radial, (perpendicular to the pivot line), loads, where the afterward pivot pin joint may carry both radial and axial thrust loads.

A "load frame within a load frame" feature may be necessary to accomplish pure axial loading in combination with circumferential loading that replicates body torsion. The axial load head 206 may be mounted on the axial-torsion reaction box 202 through the linear journal bearings assemblies 226. The axial-torsion reaction box 202 may pivot about the panel radial centerline on roller bearings 228 and 230 mounted in large pivot beams that are part of the structural self-reacting frame 214. The axial-torsion reaction box 202 may provide the circumferential reference frame that the axial loading system 208 may work within.

Historically, existing fixtures have structurally grounded the axial loading system to the same rigid frame as the shear systems. Deflection of the test panel would produce a misalignment of the axial loading system, causing an off-angle load application, resulting in a non-representative component load. Some solutions required an externally controlled anchor point to maintain the axial loading system alignment. In contrast to the existing fixtures, the axial-torsion reaction box 202 may provide both a relative reaction framework as well as transferring the application of torsion and consequently, the axial loading system 208 may be anchored directly to this rotating structure, simplifying the load application system. This may enable circumferential panel movement in shear load cases in a manner similar to what the test panel assembly 201 would experience in the fuselage barrel section 100. This configuration may also produce high internal loads at the corners of the test panel assembly 201 in shear load cases. The moment induced by the shear load may be balanced by the reaction moment at both the forward and aft ends of the panel-to-fixture interface. This geometry required the axial-torsion reaction box 202 to be very stiff in torsion. The axial load may be reacted through the center-trussed structure, to cylindrical radial-thrust roller bearings 228 in the aft pivot location. This spine running through the length of the axial-torsion reaction box 202 may provide a direct line of action for the axial load application.

The application of torsion may be accomplished via two hydraulically actuated torsion loading systems 210 applying loads to opposing torque arms in the front of the axial-torsion reaction box 202. The required actuator load may be to the sum of the load transferred to the test panel assembly 201 and the load induced by friction. To minimize the friction effects, special roller bearings 228 and 230 may be employed at the pivot points.

A closed-loop, servo-hydraulic control system may be used to apply and control loads to the test specimen. The load control system may continually monitor and maintain load applications to meet user programmed load requirements. Error and load limit tolerances may be specified to provide specimen safety. Load cells and pressure transducers may measure the loads applied by the hydraulic cylinders or pneumatic control valves. The load cell or pressure transducer output may provide the necessary feedback to the control system. Such simple and robust control system configurations may help eliminate uncertainty. It may also facilitate increased cycling speed when applying alternating load fatigue cycles, thereby reducing testing time.

Figure 12:
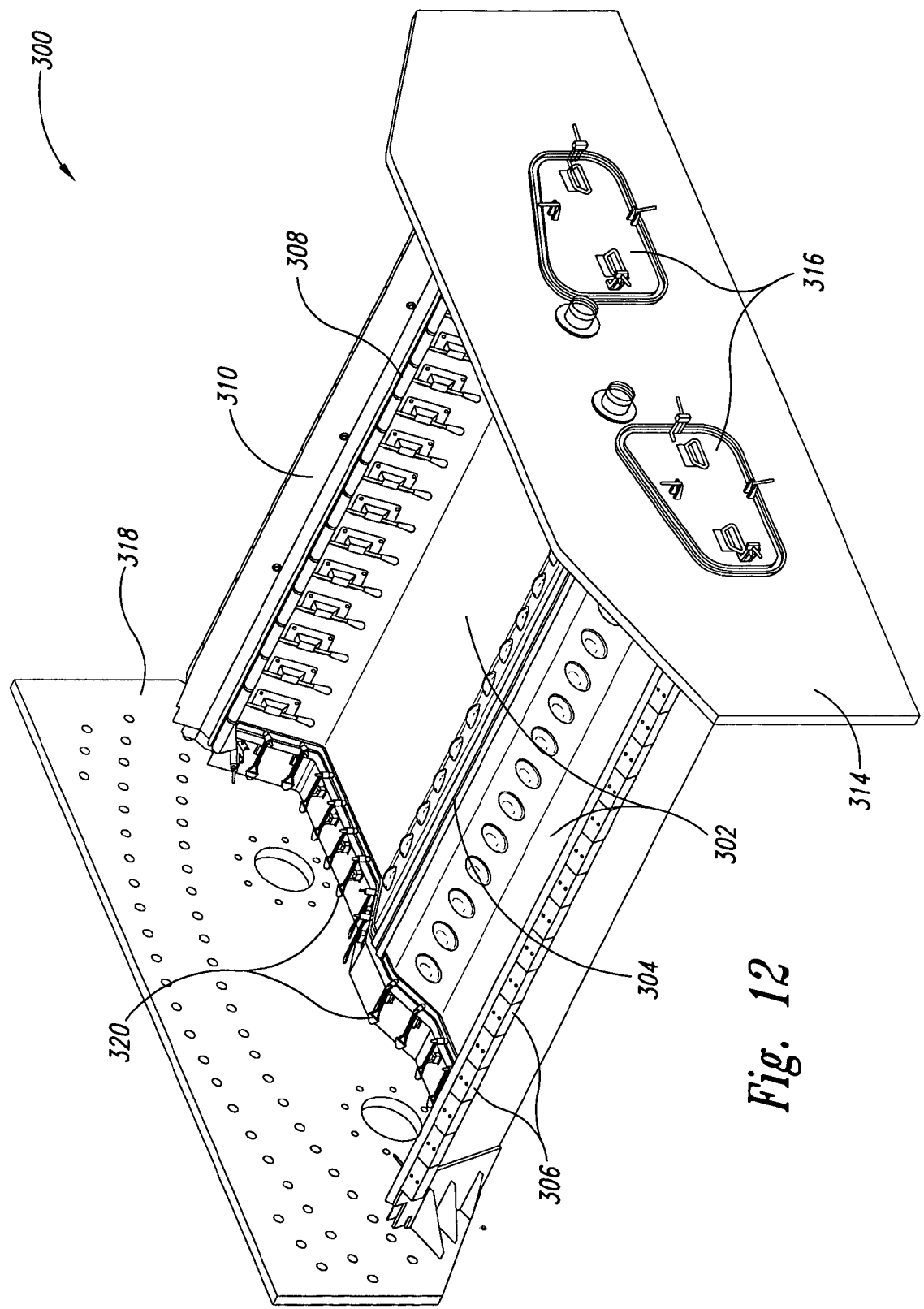
FIG. 12 is a perspective view of the plenum box assembly of the E-Fixture of FIG. 2.

FIG. 12 is a perspective view of the plenum box assembly 300 of the E-Fixture 200. As illustrated in FIG. 12, the plenum box assembly 300 may contain a pair of air pressure sealing membranes (or, equivalently, plenum box elastomeric floor) 302 that may be supported by the horizontal members of the gore section frame assemblies 248; a floor split line clamp assembly 304; hoop edge fill blocks 306; and skirt seal quick clamps 308. The sealing membrane 302 may be a rubber sheet sealed along the periphery by re-usable clamping devices that may include plenum end seal clamp assemblies 320 and skirt seal quick clamps 308. The floor split line clamp assembly 304 may allow the membrane 302 to be split to facilitate test panel installation and access to the hoop load systems 252. The axial load head bulkhead 318 and fixed reaction bulkhead assembly 314 may also serve as the closure plates for the air pressurization of the plenum box assembly 300.

Access to the interior of the plenum box assembly 300 may be provided through two portals 312 located in the fixed reaction bulkhead assembly 314. Each portal 312 may be covered by removable access hatches 316. Each test panel assembly 201 may have rubber skirts 310 bonded along the hoop edges. The rubber skirts 310 may be clamped to the sealing membrane 302 via quick clamp assemblies 308. The axial load fittings 216 may accomplish sealing at the panel ends. These features may allow for rapid installation and removal of the test panel assembly 201.

Figure 13:
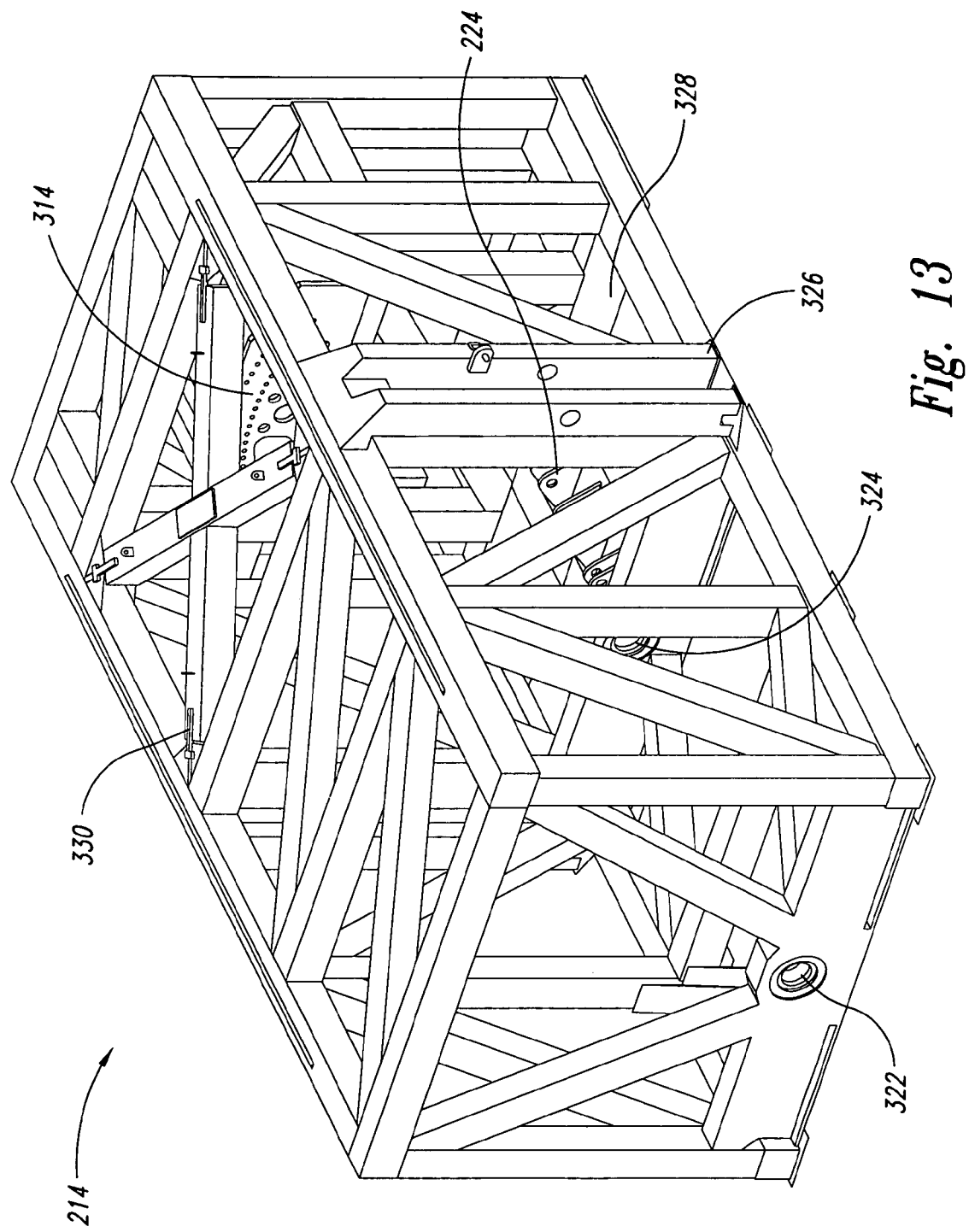
FIG. 13 is a perspective view of the structural self-reacting frame of the E-Fixture of FIG. 2.

FIG. 13 is a perspective view of the structural self-reacting frame 214 of the E-Fixture 200 of FIG. 2. As illustrated in FIG. 13, the self-reacting frame 214 may include: an aft radial-thrust pivot bearing support 322; a forward radial pivot bearing support 324; the gore pivot base 224; a torsional system support structure 326; a structural diaphragm 328; and a removable cross-brace assembly 330. No special anchor provisions are required since there is no load transfer into a structural base or floor. The stiff nature of the self-reacting frame 214 may provide good strain distribution throughout the panel test area.

The fixed reaction bulkhead assembly 314 may support the fixed end of the test panel assembly 201. The gore pivot base 224 may provide supports for the pivot pin and the gore section assemblies 220. Located at the test panel radius center, its nine supporting plates may provide shaft stiffness and reduce bending of the shaft. The pivot centerline may be aligned via precise machining within the gore pivot base 224. The gore pivot base 224 may be precisely located with respect to the fixed reaction bulkhead assembly 314 during the assembly of the reaction structure to avoid extraneous loading from non-concentric locations of the load application structures. The removable cross-brace assembly 330 may be located over the test panel bay to facilitate panel installation.

It should be understood, of course, that the foregoing relates to preferred embodiments of the invention and that modifications may be made without departing from the spirit and scope of the invention as set forth in the following claims.

We claim:

1. A device for testing a test panel assembly simulating an aircraft fuselage barrel section, comprising:
   an axial load head assembly attached to the test panel assembly via a first axial load fitting and configured to apply an axial load to the test panel assembly;
   an axial-torsion reaction box connected to the axial load head assembly via a plurality of linear journal bearing assemblies, the axial-torsion reaction box configured to be rotated by a pair of torsional loading systems to apply a torsional load to the test panel assembly;
   a gore section attached to a plurality of hoop load fittings of the test panel assembly and configured to apply an internal pressure load and a hoop load to the test panel assembly; and
   a fixed reaction box attached to the test panel assembly via a second axial load fitting and configured to remain stationary during application of loads.

2. The device of claim 1, wherein the axial load head assembly comprises:
   an axial loading system configured to generate the axial load;
   an axial-load head connected to the axial loading system and having an axial load fitting interface for the first axial load fitting; and
   a pair of over-pressure assembly portings.

3. The device of claim 1, wherein the gore section comprises:
   a plurality of gore section frame assemblies rotatably connected to a gore pivot base;
   a plurality of hoop load clevis fittings, each said hoop load clevis fitting attached to one of the plurality of gore section frame assemblies;
   a plurality of hoop load actuators mounted on one of the plurality of gore section frame assemblies;
   a plenum box assembly located between the test panel assembly and the plurality of gore section frame assemblies;
   a plurality of hoop stop assemblies, each said hoop stop assembly mounted on one of the plurality of gore section frame assemblies;
   a plurality of counter-weights for compensating weight of the plurality of gore section frame assemblies; and
   a plurality of counter-balance attachment connected to the plurality of counter-weights via a plurality of wire ropes and attached to one of the plurality of gore section frame assemblies.

4. The device of claim 3, wherein each of the plurality of hoop stop assemblies comprises:
   a stop tube;
   a pair of progressive stop disc spring assemblies located on both sides of the stop tube, respectively;
   a pair of elastomeric die springs, each said die spring located between the stop tube and one of the pair of progressive stop disc spring assemblies; and
   a bar element disposed through the stop tube, the pair of elastomeric die springs and the pair of progressive stop disc spring assemblies.

5. The device of claim 3, wherein each of the plurality of hoop load clevis fittings connected to one of the plurality of hoop load fittings via a calibrated load pin.

6. The device of claim 3, wherein the test panel assembly comprises a rubber skirt and wherein the plenum box assembly comprises:
   a pair of air pressure sealing membranes mounted on top of the plurality of gore section frame assemblies;
   a floor split line clamp assembly for clamping the pair of air pressure sealing membranes;
   a plurality of plenum end seal clamp assemblies attached to axial edges of the pair of air pressure sealing membranes;
   a plurality of hoop edge fill blocks attached to radial edges of the pair of air pressure sealing membranes; and
   a plurality of skirt seal quick clamps attached to the plurality of hoop edge fill blocks for clamping the rubber skirt.

7. The device of claim 3, further comprising a structural self-reacting frame having a plurality of truss structures, said structural self-reacting frame comprising:
   a fixed reaction bulkhead assembly secured to one of the plurality of truss structure;
   an aft radial-thrust pivot bearing support located on a first one of the plurality of truss structures;
   a forward radial pivot bearing support located on a second one of the plurality of truss structures;
   a torsion system support structure secured to a third one of the plurality of truss structures;
   a removable cross-brace assembly coupled to a fourth one of the plurality of truss structures;
   a gore pivot base secured to a fifth one of the plurality of truss structures; and a structural diaphragm located under the gore pivot base.

8. The device of claim 7, wherein the fixed reaction bulkhead assembly includes an inlet for providing air pressure to the plenum box assembly and two removable hatches covering the two access portals, respectively.

9. The device of claim 3, wherein each of the plurality of hoop load actuators is a hydraulic actuator.

10. The device of claim 1, wherein each of the pair of torsional loading systems is a hydraulic system.

11. A test panel installation, comprising:
    a curved panel having two axial composite edge bands and two radial composite edge bands, said two axial composite edge bands potted and connected to a first and second axial load fittings, respectively;
    a plurality of hoop load fittings attached to the two radial composite edge bands;
    a plurality of bonded pads attached to the curved panel;
    a plurality of frames secured to the curved panel;
    a plurality of stringers secured to the curved panel;
    a plurality of frame transition fittings for securing the plurality of frames to the curved panel; and
    a plurality of steel doublers attached to corners of the curved panel.

12. The test panel installation of claim 11, further comprising an axial load head assembly, said axial load head assembly comprising:
    an axial loading system configured to generate an axial load;

an axial-load head connected to the axial loading system and having an axial load fitting interface for the first axial load fitting; and
a pair of over-pressure frangible disk assemblies.

13. The test panel installation of claim 11, further comprising a gore section, said gore section comprising:
a plurality of gore section frame assemblies rotatably connected to a gore pivot base;
a plurality of hoop load clevis fittings, each said hoop load clevis fitting attached to one of the plurality of gore section frame assemblies and connected to one of the plurality of hoop load fittings via a calibrated load pin;
a plurality of hoop load actuators mounted on one of the plurality of gore section frame assemblies;
a plenum box assembly located between the curved panel and the plurality of gore section frame assemblies; and
a plurality of hoop stop assemblies, each said hoop stop assembly mounted on one of the plurality of gore section frame assemblies.

14. The test panel installation of claim 13, wherein the gore section comprises:
a plurality of counter-weights for compensating weight of the plurality of gore section frame assemblies; and
a plurality of counter-balance attachment connected to the plurality of counter-weights via a plurality of wire ropes and attached to one of the plurality of gore section frame assemblies.

15. The test panel installation of claim 13, wherein each of the plurality of hoop stop assemblies comprises:
a stop tube;
a pair of progressive stop disc spring assemblies located on both sides of the stop tube, respectively;
a pair of elastomeric die springs, each said die spring located between the stop tube and one of the pair of progressive stop disc spring assemblies; and
a bar element disposed through the stop tube, the pair of elastomeric die springs and the pair of progressive stop disc spring assemblies.

16. The test panel installation of claim 13, wherein the curved panel comprises a rubber skirt and wherein the plenum box assembly comprises:
a pair of air pressure sealing membranes mounted on top of the plurality of gore section frame assemblies.

17. The test panel installation of claim 16, wherein the plenum box assembly comprises:
a floor split line clamp assembly for clamping the pair of air pressure sealing membranes;
a plurality of plenum end seal clamp assemblies attached to axial edges of the pair of air pressure sealing membranes;
a plurality of hoop edge fill blocks attached to radial edges of the pair of air pressure sealing membranes; and
a plurality of skirt seal quick clamps attached to the plurality of hoop edge fill blocks for clamping the rubber skirt.

18. The test panel installation of claim 13, further comprising a structural self-reacting frame having a plurality of truss structures, said structural self-reacting frame comprising:
a fixed reaction bulkhead assembly secured to one of the plurality of truss structure;
an aft radial-thrust pivot bearing support located on a first one of the plurality of truss structures; and
a forward radial pivot bearing support located on a second one of the plurality of truss structures.

19. The test panel installation of claim 18, said structural self-reacting frame comprising:
a torsion system support structure secured to a third one of the plurality of truss structures;
a removable cross-brace assembly coupled to a fourth one of the plurality of truss structures;
a gore pivot base secured to a fifth one of the plurality of truss structures; and a structural diaphragm located under the gore pivot base.

20. The test panel installation of claim 19, wherein the fixed reaction bulkhead assembly includes one inlet for providing air pressure to the plenum box assembly and two removable access portals with hatches covering the portals, respectively.

21. The test panel installation of claim 13, wherein each of the plurality of hoop load actuators is a hydraulic actuator and wherein each of the pair of torsional loading systems is a hydraulic system.

22. A device for testing a test panel assembly simulating an aircraft fuselage barrel section, comprising:
an axial load system for generating and applying an axial load to the test panel assembly;
an axial load head connected to the axial loading system, said axial load head having an axial load fitting interface and a pair of over-pressure assembly portings;
an axial-torsion reaction box connected to the axial load head assembly via a plurality of linear journal bearing assemblies, the axial-torsion reaction box configured to be rotated by a pair of torsional loading systems to apply a torsional load to the test panel assembly;
a gore section attached to a plurality of hoop load fittings of the test panel assembly and configured to apply an internal pressure load and a hoop load to the test panel assembly; and
a fixed reaction box attached to the test panel assembly via a second axial load fitting and configured to remain stationary during application of loads.

23. The device of claim 22, wherein the gore section comprises:
a plurality of gore section frame assemblies rotatably connected to a gore pivot base;
a plurality of hoop load clevis fittings, each said hoop load clevis fitting attached to one of the plurality of gore section frame assemblies; and
a plurality of hoop load actuators mounted on one of the plurality of gore section frame assemblies.

24. The device of claim 23, wherein the gore section comprises:
a plenum box assembly located between the test panel assembly and the plurality of gore section frame assemblies; and
a plurality of hoop stop assemblies, each said hoop stop assembly mounted on one of the plurality of gore section frame assemblies.

25. The device of claim 24, wherein the gore section comprises:
a plurality of counter-weights for compensating weight of the plurality of gore section frame assemblies; and
a plurality of counter-balance attachment connected to the plurality of counter-weights via a plurality of wire ropes and attached to one of the plurality of gore section frame assemblies.

26. The device of claim 24, wherein each of the plurality of hoop stop assemblies comprises:
a stop tube;
a pair of progressive stop disc spring assemblies located on both sides of the stop tube, respectively;

a pair of elastomeric die springs, each said die spring located between the stop tube and one of the pair of progressive stop disc spring assemblies; and a bar element disposed through the stop tube, the pair of elastomeric die springs and the pair of progressive stop disc spring assemblies.

27. The device of claim 22, further comprising a structural self-reacting frame having a plurality of truss structures, said structural self-reacting frame comprising:

a fixed reaction bulkhead assembly secured to one of the plurality of truss structure, said fixed reaction bulkhead assembly including one inlet for providing air pressure to the plenum box assembly and two access portals with removable hatches covering the portals, respectively.

28. The device of claim 27, wherein the structural self-reacting frame comprises an aft radial-thrust pivot bearing support located on a first one of the plurality of truss structures;

a forward radial pivot bearing support located on a second one of the plurality of truss structures;

a torsion system support structure secured to a third one of the plurality of truss structures;

a removable cross-brace assembly coupled to a fourth one of the plurality of truss structures;

a gore pivot base secured to a fifth one of the plurality of truss structures; and a structural diaphragm located under the gore pivot base.

29. The device of claim 23, wherein each of the plurality of hoop load actuators is a hydraulic actuator and each of the pair of torsional loading systems is a hydraulic system.

30. A device for testing a test panel assembly simulating an aircraft fuselage barrel section, comprising:

an axial load system for generating axial load;

an axial load head connected to the axial loading system, said axial load head having an axial load fitting interface and a pair of over-pressure frangible disk assembly portings;

an axial-torsion reaction box connected to the axial load head assembly via a plurality of linear journal bearing assemblies, the axial-torsion reaction box configured to be rotated by a pair of torsional loading systems to apply a torsional load to the test panel assembly;

a gore section attached to a plurality of hoop load fittings of the test panel assembly and configured to apply an internal pressure load and a hoop load to the test panel assembly, said gore section comprising:

a plurality of gore section frame assemblies rotatably connected to a gore pivot base;

a plurality of hoop load clevis fittings, each said hoop load clevis fitting attached to one of the plurality of gore section frame assemblies;

a plurality of hoop load actuators mounted on one of the plurality of gore section frame assemblies;

a plenum box assembly located between the test panel assembly and the plurality of gore section frame assemblies;

a plurality of hoop stop assemblies, each said hoop stop assembly being mounted on one of the plurality of gore section frame assemblies and comprising:

a stop tube;

a pair of progressive stop disc spring assemblies located on both sides of the stop tube, respectively;

a pair of elastomeric die springs, each said die spring located between the stop tube and one of the pair of progressive stop disc spring assemblies; and a bar element disposed through the stop tube, the pair of elastomeric die springs and the pair of progressive stop disc spring assemblies;

a plurality of counter-weights for compensating weight of the plurality of gore section frame assemblies; and a plurality of counter-balance attachment connected to the plurality of counter-weights via a plurality of wire ropes and attached to one of the plurality of gore section frame assemblies; and a fixed reaction box attached to the test panel assembly via a second axial load fitting and configured to remain stationary during application of loads.

31. The device of claim 30, wherein the test panel assembly comprises a rubber skirt and wherein the plenum box assembly comprises:

a pair of air pressure sealing membranes mounted on top of the plurality of gore section frame assemblies;

a floor split line clamp assembly for clamping the pair of air pressure sealing membranes;

a plurality of plenum end seal clamp assemblies attached to axial edges of the pair of air pressure sealing membranes;

a plurality of hoop edge fill blocks attached to radial edges of the pair of air pressure sealing membranes;

a plurality of skirt seal quick clamps attached to the plurality of hoop edge fill blocks for clamping the rubber skirt; and a structural self-reacting frame having a plurality of truss structures, said structural self reacting frame comprising:

a fixed reaction bulkhead assembly secured to one of the plurality of truss structure;

an aft radial-thrust pivot bearing support located on a first one of the plurality of truss structures;

a forward radial pivot bearing support located on a second one of the plurality of truss structures;

a torsion system support structure secured to a third one of the plurality of truss structures;

a removable cross-brace assembly coupled to a fourth one of the plurality of truss structures;

a gore pivot base secured to a fifth one of the plurality of truss structures; and a structural diaphragm located under the gore pivot base.

32. A device for testing a test panel assembly simulating an aircraft fuselage barrel section, comprising:

an axial load system for generating axial load;

an axial load head connected to the axial loading system, said axial load head having an axial load fitting interface and a pair of over-pressure frangible disk assembly portings;

an axial-torsion reaction box connected to the axial load head assembly via a plurality of linear journal bearing assemblies, the axial-torsion reaction box configured to be rotated by a pair of torsional loading systems to apply a torsional load to the test panel assembly;

a gore section attached to a plurality of hoop load fittings of the test panel assembly and configured to apply an internal pressure load and a hoop load to the test panel assembly, said gore section comprising:

a plurality of gore section frame assemblies rotatably connected to a gore pivot base;

a plurality of hoop load clevis fittings, each said hoop load clevis fitting attached to one of the plurality of gore section frame assemblies;

a plurality of hoop load actuators mounted on one of the plurality of gore section frame assemblies;

a plenum box assembly located between the test panel assembly and the plurality of gore section frame assemblies;

a plurality of hoop stop assemblies, each said hoop stop assembly mounted on one of the plurality of gore section frame assemblies;

a plurality of counter-weights for compensating weight of the plurality of gore section frame assemblies; and a plurality of counter-balance attachment connected to the plurality of counter-weights via a plurality of wire ropes and attached to one of the plurality of gore section frame assemblies;

a fixed reaction box attached to the test panel assembly via a second axial load fitting and configured to remain stationary during application of loads; and a structural self-reacting frame having a plurality of truss structures, said structural self-reacting frame comprising:
- a fixed reaction bulkhead assembly secured to one of the plurality of truss structure;
- an aft radial-thrust pivot bearing support located on a first one of the plurality of truss structures;
- a forward radial pivot bearing support located on a second one of the plurality of truss structures;
- a torsion system support structure secured to a third one of the plurality of truss structures;
- a removable cross-brace assembly coupled to a fourth one of the plurality of truss structures;
- the gore pivot base secured to a fifth one of the plurality of truss structures; and
- a structural diaphragm located under the gore pivot base.

33. A method for applying combined loadings to a test panel assembly to simulate airframe real flight loads on a fuselage barrel section, said method comprising:

loading a test panel assembly to a test fixture to produce a loaded test panel assembly, wherein the test fixture includes a gore section, an axial load head assembly, and an axial-torsion reaction box, and wherein loading includes attaching a plurality of hoop load fittings of the test panel assembly to the gore section, attaching the axial load head assembly to the test panel assembly via a first axial load fitting, and connecting an axial-torsion reaction box to the axial load head assembly via a plurality of linear journal bearing assemblies;

applying a circumferential hoop load to the loaded test panel assembly via the gore section of the test fixture to simulate a real internal cabin pressure;

applying an axial load to the loaded test panel assembly via the axial load head assembly to simulate a real axial load;

applying a shear load to the loaded test panel assembly via the axial-torsion reaction box to simulate a real shear load; and attaching the loaded test panel assembly to a fixed reaction box to keep the loaded test panel in a stationary position while applying a circumferential hoop load, applying an axial load, and applying a shear load.

34. The method of claim 33, further comprising: applying an air pressure to the loaded test panel assembly via a plenum box assembly of the test fixture to simulate a real internal cabin pressure.

* * * * *